United States Patent [19]

Hosterman et al.

[11] Patent Number: 5,277,194
[45] Date of Patent: Jan. 11, 1994

[54] BREATHING MONITOR AND STIMULATOR

[76] Inventors: Craig Hosterman, 131 NW. 4th St. #263; Alvin W. Smith, 26833 Sulphur Springs Rd., both of Corvallis, Oreg. 97330

[21] Appl. No.: 710,506

[22] Filed: Jun. 4, 1991

Related U.S. Application Data

[63] Continuation-in-part of Ser. No. 304,670, Jan. 31, 1989, abandoned.

[51] Int. Cl.⁵ .................... A61B 5/08; A61H 31/00
[52] U.S. Cl. .................................. 128/721; 128/28
[58] Field of Search ........................... 128/721-

[56] References Cited

U.S. PATENT DOCUMENTS

| | | |
|---|---|---|
| 1,619,886 | 3/1927 | Ryan ............................ 128/721 |
| 2,989,050 | 6/1961 | Mayo . |
| 3,333,581 | 8/1967 | Robinson et al. . |
| 3,483,861 | 12/1969 | Tiep . |
| 3,545,429 | 12/1970 | Pelta et al. . |
| 3,782,368 | 1/1974 | Reibold . |
| 3,795,240 | 3/1974 | Frank . |
| 3,802,417 | 4/1974 | Lang . |
| 3,831,586 | 8/1974 | Petit . |
| 3,882,847 | 5/1975 | Jacobs . |
| 3,888,240 | 6/1975 | Reinhold, Jr. . |
| 3,911,899 | 10/1975 | Hattes . |
| 3,950,799 | 4/1976 | Frank . |
| 3,965,893 | 6/1976 | Ragailler . |
| 3,998,209 | 12/1976 | Macvaugh . |
| 4,102,332 | 7/1978 | Gessman . |
| 4,169,462 | 10/1979 | Strube ............................ 128/721 |
| 4,413,620 | 11/1983 | Tucker ............................ 128/134 |
| 4,420,001 | 12/1983 | Hearne ............................ 128/724 |
| 4,433,693 | 2/1984 | Hochstein ............................ 128/721 |
| 4,506,666 | 3/1985 | Durkan . |
| 4,576,179 | 3/1986 | Manus ............................ 128/671 |
| 4,602,643 | 7/1986 | Dietz ............................ 128/721 |
| 4,619,270 | 10/1986 | Margolis et al. ............................ 128/721 |
| 4,694,839 | 9/1987 | Timme ............................ 128/721 |
| 4,696,307 | 9/1987 | Montigieux ............................ 128/721 |
| 4,715,367 | 12/1987 | Crossley ............................ 128/136 |
| 4,813,427 | 3/1989 | Schlaefke et al. ............................ 128/671 |
| 4,813,428 | 3/1989 | Muraki et al. ............................ 128/721 |
| 4,830,008 | 5/1989 | Meer ............................ 128/721 |
| 4,928,674 | 11/1988 | Halperin et al. ............................ 128/28 |
| 4,948,899 | 8/1990 | Sugiyama et al. ............................ 128/721 |
| 4,998,528 | 3/1991 | Erhardt et al. ............................ 128/721 |
| 5,022,402 | 6/1991 | Schieberl et al. ............................ 128/721 |
| 5,056,505 | 10/1991 | Warwick ............................ 128/28 |
| 5,088,561 | 2/1992 | Niewisch ............................ 128/721 |

FOREIGN PATENT DOCUMENTS

| | | |
|---|---|---|
| 1225889 | 8/1987 | Canada . |
| 2853252 | 6/1980 | Fed. Rep. of Germany . |
| 522565 | 4/1955 | Italy ............................ 128/721 |
| US85/01156 | 6/1985 | PCT Int'l Appl. . |

OTHER PUBLICATIONS

*Insight*, Mar. 27, 1989 issue, p. 58, "Device Helps Prevent Premature Birth".

*Primary Examiner*—Randall L. Green
*Assistant Examiner*—K. M. Reichle
*Attorney, Agent, or Firm*—Cahill, Sutton & Thomas

[57] ABSTRACT

Apparatus worn about the chest of a user monitors the breathing pattern and upon occurrence of an abnormal breathing pattern stimulates the respiratory reflexes to urge resumption of the normal breathing patterns. Alarms may be actuated upon detection of an abnormal breathing pattern.

15 Claims, 2 Drawing Sheets

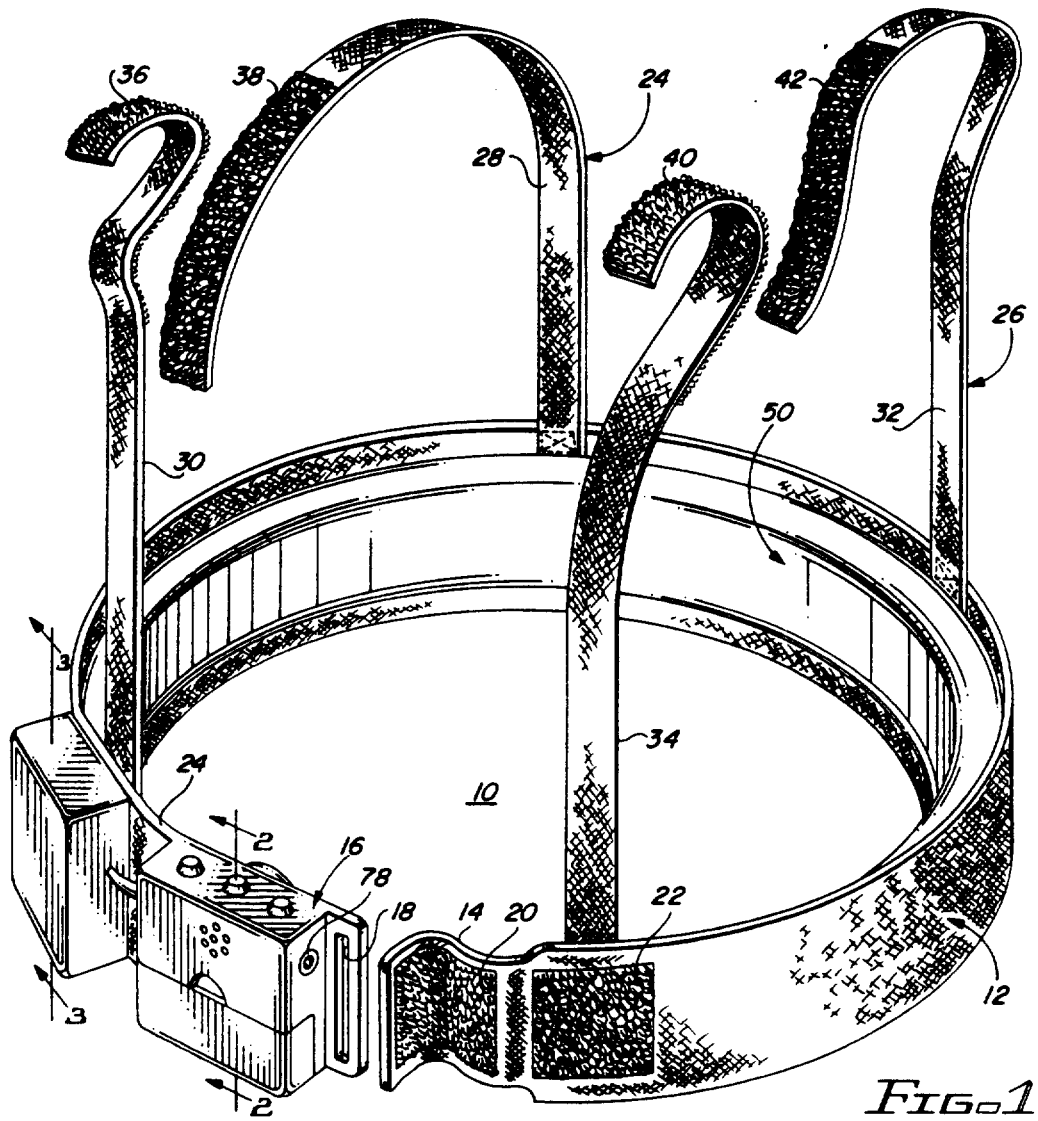
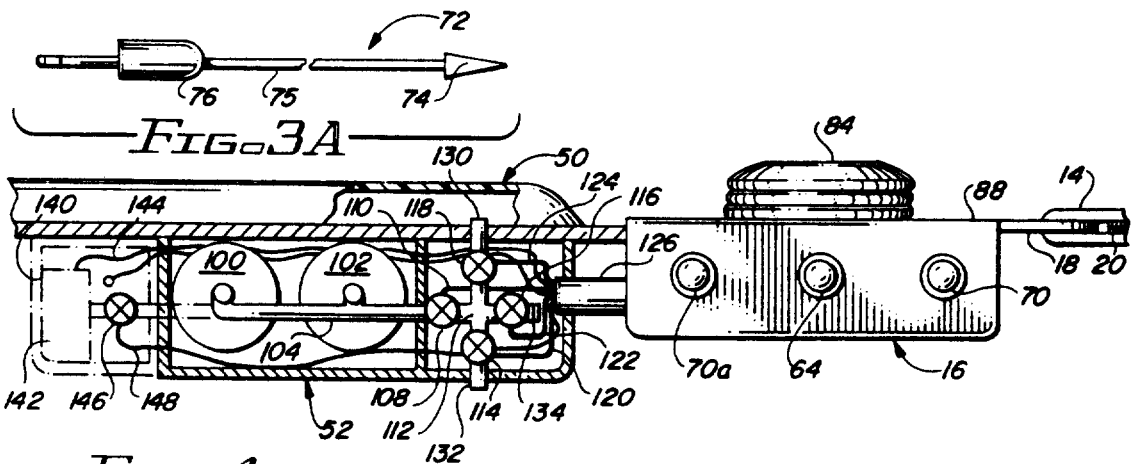

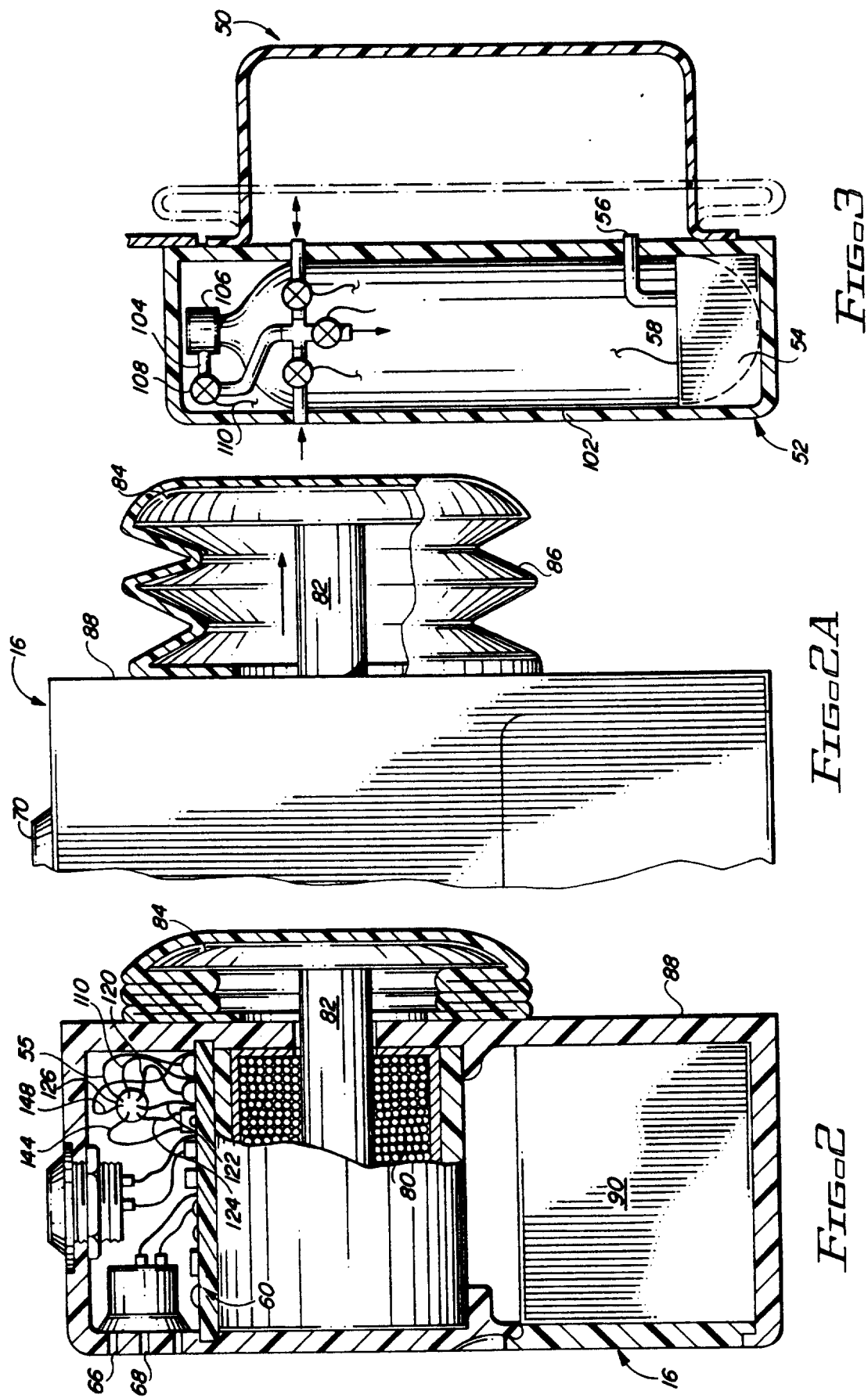

BREATHING MONITOR AND STIMULATOR

CROSS REFERENCE TO RELATED APPLICATION

The present application is a continuation-in-part application of U.S. patent application Ser. No. 304,670 filed Jan. 31, 1989 and entitled "Breathing Monitor and Stimulator" describing an invention by the present inventors, and now abandoned.

BACKGROUND OF THE INVENTION

1. Field of the Invention

The present invention relates to portable breathing stimulators and, more particularly, to apparatus for detecting arrhythmic breathing patterns and stimulating a resumption of breathing after cessation of breathing is detected.

2. Description of Prior Art

Three types of apnea have been identified by the medical community. These are central nervous system apnea, obstructive apnea and apnea that is a combination of the two. Generally, apnea does not result in breathing failure but more often a disturbance of the normal breathing pattern to rouse a person from deep sleep; this may occur hundreds of times per night. Sudden Infant Death Syndrome is another phenomenon that appears to have attributes of apnea associated with it. The prevalence of apnea is not known due to the difficulty in monitoring the quality of sleep. Moreover, persons who may suffer feelings of general nonspecific fatigue usually tend to attribute it to factors other than apnea caused.

Over the years, various devices have been developed for the purpose of monitoring and/or detecting a change in a person's breathing pattern. Upon such detection, indicia may be generated in the manner of a warning or alarm signal. These devices are variously attached to a person under observation. Moreover, the devices may be essentially self contained or they may be connected to an external power source, external warning indicia or developed as part of an enclosure within which the person, usually a baby, is being monitored.

Various other devices have been developed for detecting a change in breathing rhythm, whether sporadic or non existent. Upon such detection, an apparatus may be energized or actuated to stimulate resumption of a normal breathing pattern. These other devices are not intended to be self contained and body mounted; instead, these other devices, being intended primarily for infants, are mounted in conjunction with the structure defining the place for sleeping.

SUMMARY OF THE INVENTION

The present invention detects apnea induced breath stoppage resulting from a sleep disorder, rather than a breathing disorder and the invention will automatically commence stimulation of the respiratory reflexes to attempt to cause resumption of a proper breathing pattern. Preferably, the user is not disturbed sufficiently to cause awakening; to permit the user to remain in deep sleep is the ultimate goal. A secondary mechanism is employed to rhythmically compress and release the rib cage, diaphragm and/or abdomen and mechanically induce inhalation and exhalation in the event proper breathing is not resumed in response to reflexive action. Various signal generating circuitry provides visual and/or audible indicia responsive to normal breathing, abnormal breathing or the absence of breathing. Preferably, the device is self contained and body worn to avoid limiting the monitoring and stimulating functions to any given location of use.

It is therefore a primary object of the present invention to provide apparatus for continuously monitoring the normal breathing pattern and stimulating resumption of such normal pattern in the event of an abnormal breathing pattern.

Another object of the present invention is to provide apparatus for automatically stimulating the respiratory reflexes upon cessation of breathing.

Still another object of the present invention is to provide a self-contained, portable, body-worn apparatus for monitoring the breathing pattern and generating a signal upon detection of an abnormality in the pattern.

Yet another object of the present invention is to provide apparatus for detecting cessation of breathing and, upon such detection, mechanically compress and relax a user's rib cage, diaphragm and/or abdomen to induce airflow into and out of the lungs.

A further object of the present invention is to provide apparatus for detecting cessation of breathing and upon such detection stimulating the respiratory reflexes to bring about resumed breathing.

A still further object of the present invention is to provide a method for monitoring a user's breathing pattern and stimulating resumption of breathing upon cessation.

A yet further object of the present invention is to provide a method for detecting cessation of breathing and, upon such detection, mechanically force an outflow and inflow of air through the lungs or stimulate the respiratory reflexes to bring about a normal breathing pattern.

A yet further object of the present invention is to provide a method for establishing a data base for a patient's breathing pattern.

These and other objects of the present invention will become apparent to those skilled in the art as the description thereof proceeds.

BRIEF DESCRIPTION OF THE DRAWINGS

The present invention will be described with greater specificity and clarity with reference to the following drawings, in which:

FIG. 1 is a perspective view of apparatus for detecting apnea and stimulating resumption of breathing;

FIG. 2 is a cross sectional view taken along lines 2—2, as shown in FIG. 1;

FIG. 2A is a side view illustrating extension of a plunger for stimulating respiratory reflexes;

FIG. 3 is a partial cross sectional view taken along lines 3—3, as shown in FIG. 1;

FIG. 3a illustrates a representative probe for use in collecting oximetry data; and FIG. 4 is a partial top view of the apparatus.

DESCRIPTION OF THE PREFERRED EMBODIMENT

There are presently three types of apnea identified by the medical community: central nervous system apnea, obstructive apnea and apnea that is a combination of the two.

Members of the medical community believe apnea may be more prevalent than the extent identified. Part of this uncertainty is a function of the difficulty in monitoring large numbers of people during their sleep, which difficulty would be overcome with use of the present invention. Because the apparatus will continuously monitor and analyze the breathing rhythm of a user, it may be of benefit to persons who have suffered grave injuries or are medicated with drugs that may have secondary effects on breathing. Should there occur a cessation of breathing or an arrhythmic breathing episode, an alarm would sound immediately. This feature may be of particular importance with respect to patients who have been given certain of the new pain medication injections. Moreover, many persons who have feelings of general nonspecific fatigue may be totally unaware that these feelings could be apnea caused.

Sudden Infant Death Syndrome (SIDS) is a little understood phenomenon that appears to have some attributes of apnea associated with it. While the primary intended use of the present invention is that of treating apnea disorders when a patient is away from medical personnel, the use of the invention in preventing death due to SIDS appears feasible and realistic. The recording function of the present invention would be of assistance in accumulating data related to an infant's breathing history for research and analysis purposes.

By continuously monitoring the breathing rhythm of a person and storing data reflective thereof for a period of time, the data can be subsequently analyzed and diagnosis may be performed. Necessarily, the monitoring apparatus must be relatively easy to use, not uncomfortable and be of minimum impediment to normal activities. Where there is a serious potential of breathing stoppage, the monitoring function must also serve a detection function of such stoppage. Upon detection of breathing stoppage, alarms may be actuated but, more importantly, immediate stimulation of the respiratory reflexes must occur. Should reflexive breathing not result, the rib cage, diaphragm and/or abdomen must be repetitively compressed and released to induce inhalation and exhalation until such time as normal breathing resumes or until medical assistance is available.

Referring particularly to FIG. 1, there will be described a present embodiment of apparatus 10 for monitoring the breathing rhythm; detecting cessation of breathing and stimulating resumption of breathing upon cessation. The apparatus includes a band 12 for placement about a user's chest. End 14 of the band may be detachably attached to monitoring device 16 by inserting the end through a slot 18 extending from the monitoring device and folding the end upon itself to engage elements 20,22 of hook and loop fastening means with one another; such fastening means may be of the type sold under the trademark VELCRO. End 24 of the band may be directly attached to the monitoring device as illustrated in FIG. 1. The correct vertical position of band 12 may be established by shoulder straps 24,26 formed of segments 28, 30 and 32, 34, respectively. These pairs of segments may be adjustably secured to one another by further elements of hook and loop fastening means formed of paired elements 36, 38 and 40, 42.

An inflatable bladder 50, as shown in FIGS. 1, 3 and 4, is disposed on the interior side of band 12. The pressure variance within this bladder is reflective of the expansion and contraction of a user's chest resulting from inhalation and exhalation. To ensure accurate translation of chest movement to a change in pressure within bladder 50, band 12 must be of sufficiently rigid and of generally non-conformable material to minimize, i.e. resist, lateral and longitudinal expansion, i.e. deflection and bending, in response to chest movement and any induced pressure variations within the bladder. Moreover, the band must be sufficiently stiff to provide a solid brace or support for operation of the plunger, i.e. vertical bending of the band. To ensure correct tautness of band 12 about a user's chest or abdomen, a tensioning device could be incorporated in the band or as part of an interface between monitoring device 16 and the band. Such a tensioning device may be pneumatic, hydraulic mechanical, or electrical or a combination thereof.

Monitoring device 16 will be described in further detail with particular reference to FIGS. 1, 2 and 4. The monitoring device may include an integrally formed or segregated pneumatic module 52 (as shown). The module may include a pressure sensitive transducer 54 in fluid communication with bladder 50 through a conduit 56. By such interconnection, the transducer will sense the pressure within the bladder and generate a signal reflective thereof or a change in pressure. The signal generated by transducer 54 is transmitted through an electrical conductor 58 to an electrical circuit representatively illustrated and identified by reference numeral 60. The circuit will act upon the signal emitted by the transducer to compare it with a preset norm or standard reflective of normal breathing of a user. In the event the normal rhythm is interrupted, modified or terminated, a signal is generated by circuit 60 to activate either an audible signal generator 62 or a visually perceivable indicator 64 or both. The sound generated by generator 62 is emitted through apertures 66 formed in wall 68, of monitoring device 16. To provide a user with assurance of proper operation of apparatus 10, a visually perceivable indicator 70 may be energized to reflect such operation. Indicator 70a may be employed for ancillary purposes.

To further expand the usefulness of monitoring device 16, an oximetry device 72 (see FIG. 3a) could be incorporated to assist in the analysis of the data provided by a microprocessor. During use of the present invention with oximetry components, the monitoring of the blood oxygenation could be performed by a sensor 74 attached to another part of the user's body, such as a finger. Necessarily, electrical conductor 75 would interconnect the oximetric sensor with the components of circuit 60 in monitoring device 16 through plug 76 and socket 78. Transcutaneous electrical stimulation of muscles or nerves to cause breathing to restart can be initiated with known apparatus.

Upon cessation of breathing or other similar emergency created by a breathing rhythm change and sensed by transducer 54, circuit 60 may energize solenoid 80. Solenoid 80 includes a plunger 82 which is axially translated upon energization of the coils of the solenoid. Referring specifically to FIGS. 2 and 2A, the anterior end of the plunger includes a head 84 of slightly cushioned material. It is expected that the head may be sized between 1" and 1¼" in diameter. To preclude dirt, foreign material, body fluids or other potentially damaging elements from intruding into monitoring device 16, a bellows 86 may interconnect head 84 with case 88 of the monitoring device to shield plunger 82 and the related aperture in the case.

Axial translation of plunger 82, which may be in the range of 3", provides a pressure stimulus to Herring-Brewer and/or other respiratory reflex triggers. The resulting variations in intra-thoracic pressure will tend to trigger commencement of the normal breathing function. Power for circuit 60 and the associated electrically actuatable devices may be provided by a battery pack 90 lodged within the lower part of case 88 of the monitoring device.

While the use of a plunger and solenoid is an effective and relatively low cost means for delivering a pressure stimulus, other mechanisms, such as a lead screw coupled to an electric motor, hydraulically actuated pistons and the like could be used.

Bladder 50 performs a primary function of generating a signal responsive to the breathing rhythm of a user. This signal is developed by the varying pressure within the bladder resulting from expansion and contraction of the user's chest. The varying pressure is conveyed to transducer 54 via conduit 56, which conduit is in fluid communication with the internal volume of the bladder, as shown in FIG. 3. The varying pressure is sensed by the transducer and a corresponding electrical signal is generated. The generated signal is conveyed to circuit 60 through electrical conductor 58. In the event of cessation of breathing, the bladder could be used as a repetitively actuated compressive device for alternately compressing and relaxing the chest, diaphragm and/or abdomen which would result in involuntary compression and expansion of a user's lungs. Accordingly, a mechanized apparatus for inducing breathing is provided. Cyclic operation of bladder 50 can be accomplished with mechanisms presently well known and incorporatable with monitoring device 16 by those skilled in the relevant art. For example, module 52 may include one or more small high pressure air or gas cylinders 100,102 interconnected by conduit 104. The conduit is in fluid communication with each of the cylinders through a fitting 106 or the like. A valve 108 controls the flow from the cylinders through conduit 104. The valve may be of a solenoid actuated type of valve energized by an electrical signal on conductor 110. The conductor is interconnected with circuit 60. A cross connector 112 interconnects valve 108 with each of valves 114, 116 and 118, which valves may be solenoid actuated valves energized by conductors 120, 122 and 124, respectively. These conductors are also connected to circuit 60. Conductors 110, 120, 122 and 124 may be housed within a sheath 126 interconnecting module 52 with monitoring device 16. A conduit 130 extends from valve 118 into fluid communication with the interior of bladder 50. Conduit 132 may serve as a fill tube for pressurizing or refilling cylinders 100, 102 and/or bladder 50. Conduit 134 may serve as an exhaust conduit for relieving pressure within bladder 50.

To extend the availability of a supply of air or gas under pressure, a pump 140 may be disposed within module 52. The pump includes an electrically energized actuator 142 for operating the pump to develop a source of compressed air. Power and control for the pump may be provided through conductor 144, which conductor is connected to circuit 60. A valve 146, which may be solenoid operated and energized through conductor 148 extending from circuit 60, controls outflow from actuator 142 into conduit 104.

In operation, in response to control signals generated by circuit 60, valves 108, 116 and 118 are selectively actuated to channel a flow of air/gas under pressure into bladder 50 to expand the bladder and cause compression/contraction of the user's chest. Subsequent to expansion of the bladder, valve 116 may be opened with simultaneous closing of valve 108 and reopening of valve 118 to permit exhausting of the air/gas from within the bladder, resulting in partial or complete collapse of the bladder. Upon closing of valve 116 and reopening of valve 108, bladder 50 would be refilled to begin the next cycle. Upon transducer 54, or other device, sensing a low pressure in either of cylinders 100 or 102, ancillary indicator 70a may be energized. Such low pressure sensing would provide an indication of the necessity to replace cylinders 100, 102; alternatively, the low pressure sensing may be used to trigger pump 140 to refill and repressurize the cylinders. While a pneumatic system has been described in detail, it is to be understood that a pressurized hydraulic system could also be employed to repetitively fill and evacuate bladder 50. However, due to the inertia of the hydraulic fluid used, rapidity of expansion and contraction of the bladder may be compromised.

Should apparatus 10 not be limited to a self contained portable unit, conduit 132 could extend from monitoring device 52 to external sources of air, gas or other fluid under pressure to serve as the power source for rhythmically inflating and deflating bladder 50.

As illustrated in FIG. 3, bladder 50 would be in the range of 6" wide or of a width compatible with a user and of a girth sufficient to match the chest size of the user. The thickness of the bladder, when inflated, would be in the range of ¼" to ¾". When bladder 50 is used for the purposed of compressing and expanding the chest, the bladder would change in profile from the expanded state illustrated by the solid lines in FIG. 3 to the state illustrated by the dashed lines. Since the position of band 12 is vertically maintained by shoulder straps 24,26, the lack of grip of the bladder about the chest during deflation would not result in dropping or other displacement of band 12 from its intended vertical position about the chest.

In a more sophisticated version of monitoring device 16, a microprocessor of a type presently available could be incorporated as part of circuit 60 to serve as a data bank for collecting information reflective of the breathing rhythm of a user. This data could be subsequently downloaded at a convenient time into a computer. The data, in its raw form or converted to graphs or tables, could be displayed on a video monitor or reproduced by a printer.

From the above description, it will become apparent that apparatus 10 is capable of continuously monitoring the breathing rhythm of a user for subsequent analysis of any abnormalities indicative of medical or health problems that may be present. Upon cessation of breathing by the user, this state would be immediately detected and an involuntary respiratory reflex would be induced to obtain a resumption of breathing. In the event resumption did not occur, a mechanically forced contraction and involuntarily induced expansion of the lungs would be initiated to ensure a continuing air inflow and outflow through the lungs.

While the principles of the invention have now been made clear in an illustrative embodiment, there will be immediately obvious to those skilled in the art many modifications of structure, arrangement, proportions, elements, materials and components used in the practice of the invention which are particularly adapted for specific environments and operating requirements without departing from those principles.

We claim:

1. Apparatus for monitoring a breathing pattern of a user and for stimulating resumption of the normal breathing pattern upon occurrence of an abnormal breathing pattern, said apparatus compressing in combination:
   a) a bladder for providing pressure changes in response to inhalation and exhalation of the user;
   b) means for supporting said bladder, said supporting means including a band, said band being attachable about a torso of the user for positioning said bladder adjacent the torso, said band being sufficiently rigid and generally non-conformable to resist deflection and bending in response to inhalation and exhalation by the user and any induced pressure variations within said bladder, said supporting means further including means for maintaining said band positioned upon the torso irrespective of pressure variations within said bladder;
   c) means disposed upon said supporting means for pressurizing and depressurizing said bladder;
   d) monitoring means secured to said supporting means for sensing a normal pattern of pressure changes present in said bladder in response to normal inhalation and exhalation by the user and for generating a trigger signal in response to a sensed abnormal pattern of pressure changes; and
   e) means responsive to the trigger signal for urging resumption of the normal breathing pattern, said urging means including means for cyclicly actuating said pressurizing and depressurizing means to repetitively pressurize and depressurize the bladder to compress and to allow expansion of the torso to induce exhalation and inhalation, respectively.

2. The apparatus as set forth in claim 1 wherein said urging means further includes a rectilinearly translatable plunger.

3. The apparatus as set forth in claim 1 wherein said monitoring means includes a transducer for sensing the pressure within said bladder.

4. The apparatus as set forth in claim 3 including a source of electrical power supported by said band for energizing said monitoring means and said urging means.

5. The apparatus as set forth in claim 1 wherein said pressurizing and depressurizing means comprises a source of compressed gas and means for selectively interconnecting said bladder with said source of compressed gas.

6. The apparatus as set forth in claim 5 further including means disposed on said supporting means for replenishing said source of compressed gas.

7. The apparatus as set forth in claim 1 wherein said monitoring means includes an oximetric sensor for augmenting a determination of the presence of the normal breathing pattern.

8. Apparatus for monitoring a breathing pattern of a user and for stimulating resumption of a normal breathing pattern upon occurrence of an abnormal breathing pattern, said apparatus compressing in combination:
   a) a bladder for providing pressure changes in response to inhalation and exhalation of the user;
   b) means for supporting said bladder, said supporting means including a band, said band being attachable about a torso of the user for positioning said bladder adjacent the torso, said band being sufficiently rigid and generally non-conformable to resist deflection and bending in response to inhalation and exhalation by the user and any induced pressure changes within said bladder, said supporting means further including means for maintaining said band positioned upon the torso irrespective of pressure variations within said bladder;
   c) means disposed upon said supporting means for pressurizing and depressurizing said bladder;
   d) monitoring means secured to said supporting means for sensing a nonmoral pattern of pressure changes present in said bladder in response to normal inhalation and exhalation by the user and for generating a trigger signal in response to a sensed abnormal pattern of pressure changes; and
   e) means responsive to the trigger signal for urging resumption of the normal breathing pattern, including a rectilinearly translatable plunger for applying intra-thoracic pressure to a respiratory trigger of the user to stimulate the normal breathing pattern and means for supporting said plunger upon said band.

9. The apparatus as set forth in claim 8 wherein said plunger includes a head.

10. The apparatus as set forth in claim 8 wherein said urging means further includes solenoid means for operating said plunger.

11. Apparatus for detecting breathing and cessation of breathing of a patient and for stimulating resumption of breathing by the patient upon detection of cessation of breathing, said apparatus comprising in combination:
   a) a band attachment about a torso of the patient, said band including an inner surface for placement in juxtaposed relationship with the torso of the patient upon mounting of said band;
   b) means for maintaining said band positioned about the torso of the patient;
   c) a bladder secured to said inner surface for placement adjacent the torso of the patient upon mounting said band upon the patient, said bladder for providing pressure changes in response to inhalation and exhalation by the patient, said band being sufficiently rigid and generally non-conformable to resist deflection and bending in response to inhalation and exhalation by the patient and any induced pressure changes within said bladder;
   d) means disposed upon said band for pressurizing and depressurizing said bladder;
   e) pressure responsive monitoring means disposed upon said band for sensing a normal pattern of pressure changes induced by said bladder in response to normal inhalation and exhalation by the patient and for generating a trigger signal in response to a sensed abnormal pattern of pressure changes resulting from abnormal inhalation and exhalation by the patient; and
   f) means responsive to the trigger signal for cyclicly actuating said pressurizing and depressurizing means to repetitively pressurize and depressurize the bladder to compress and to allow expansion of the torso to induce exhalation and inhalation, respectively, and the resumption of a normal breathing pattern.

12. The apparatus as set forth in claim 11 further including means supported upon said band for stimulating a respiratory reflex in the patient.

13. The apparatus as set forth in claim 12 wherein said stimulating means comprises a source of electric power, an electrically-actuated solenoid and a plunger responsive to said solenoid for applying intra-thoracic pressure to stimulate breathing, each of said source, said solenoid and said plunger being mounted upon said band.

14. The apparatus as set forth in claim 11 including indicia responsive to said monitoring means for reflecting the presence of the normal and an abnormal breathing pattern.

15. The apparatus as set forth in claim 11 wherein said maintaining means includes a pair of shoulder straps and means for adjusting said shoulder straps to reposition said band about the patient's torso.

* * * * *